United States Patent [19]

Komura et al.

[11] 4,106,989

[45] Aug. 15, 1978

[54] THERMOSTABLE CELLULASE AND A METHOD FOR PRODUCING THE SAME

[75] Inventors: Ichiro Komura, Kawasaki; Takeyoshi Awao; Kazuhiko Yamada, both of Fujisawa, all of Japan

[73] Assignee: Ajinomoto Co., Inc., Tokyo, Japan

[21] Appl. No.: 791,013

[22] Filed: Apr. 26, 1977

[30] Foreign Application Priority Data

Apr. 30, 1976 [JP] Japan .................................. 51-49463

[51] Int. Cl.$^2$ ............................................ C12D 13/10
[52] U.S. Cl. ....................................... 195/62; 195/65; 195/33
[58] Field of Search ................... 195/62, 65, 66 R, 33

[56] References Cited
PUBLICATIONS

Stutzenberger, Applied Microbiology, Aug. 1971, pp. 147–152.
Coutts et al, Applied and Environmental Microbiology, Jun. 1976, pp. 819–825, 1976.
Eriksson et al, European Journal of Biochemistry, vol. 51, pp. 213–218 (1975).

*Primary Examiner*—Lionel M. Shapiro
*Attorney, Agent, or Firm*—Hans Berman

[57] ABSTRACT

The present invention relates to a newly found thermostable cellulase of Sporotrichum cellulophilum and a method for producing the same.

5 Claims, 3 Drawing Figures

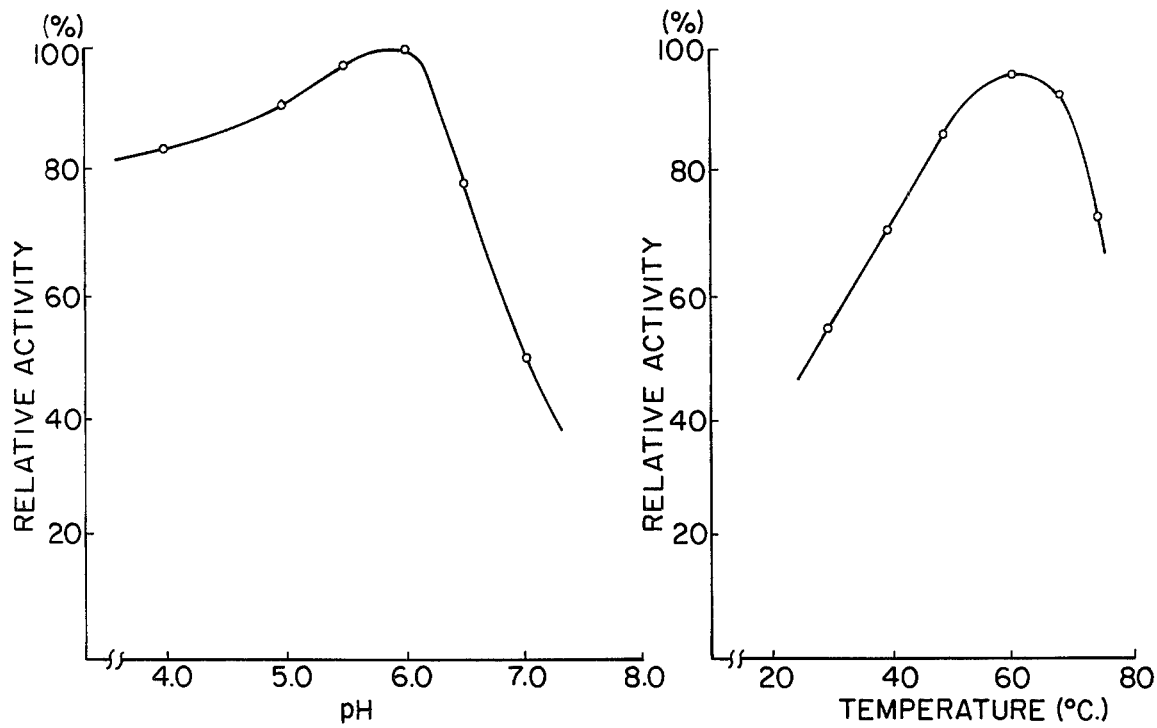
FIG.1
FIG.2
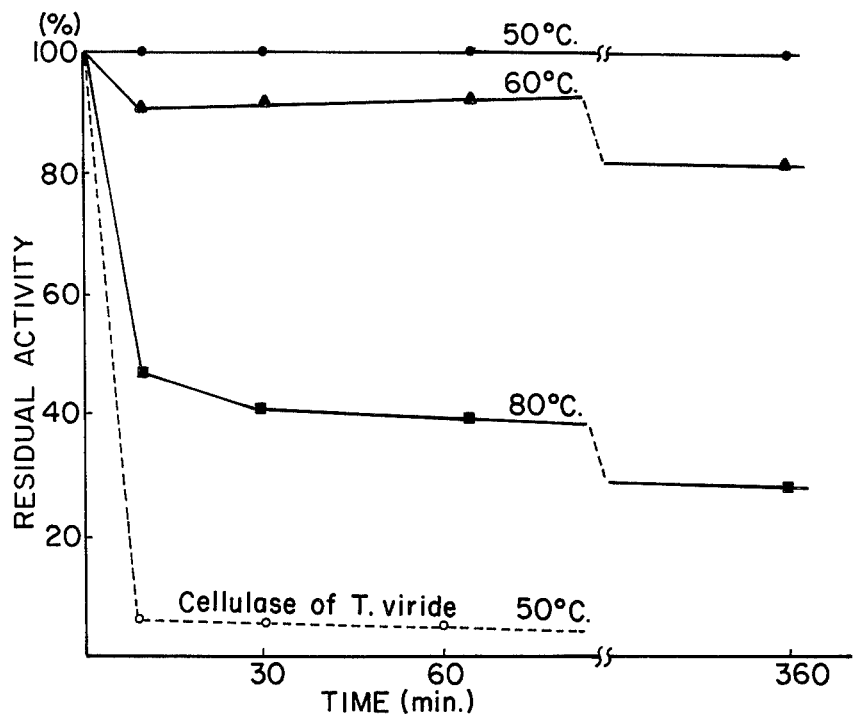
FIG.3

THERMOSTABLE CELLULASE AND A METHOD FOR PRODUCING THE SAME

As one of the earth's most abundant renewable organic chemicals, the importance of cellulose as a potential source of food, chemicals, carbon source for various fermentations, and the like is becoming increasingly recognized.

Tremendous quantities of waste cellulosic materials are available which can be roughly categorized as municipal wastes, industrial wastes such as paper mill effluents, sawdust and sludges, and agricultural wastes such as grasses, straws, bagasses, hulls, stalks and pomaces. While most such materials are currently burned, buried, or otherwise discarded without recycling, proper treatment could change them from liabilities into assets.

For hydrolysis of solid cellulose by enzyme, cellulase which contains $C_1$ factor is required and many kinds of microorganisms belonging to basidiomycetes, bacteria, actinomycetes and fungi such as Trichoderma viride, Penicillum pusillum, Chrysosporium pruinosum produce such a cellulase. Among them, Trichoderma viride is known to be the most reliable producer of stable cellulase complex including $C_1$ factor.

Although the other fungi, Chrysosporium pruinosum (which is a synonym of Sporotrichum pruinosum) and Penicillium pusillum produce filtrates having a high $C_1$ factor, the activity is less stable, and inferior to that of trichoderma viride filtrate as described by M. Mandels & J. Weber: ADVANCES IN CHEMISTRY SERIES, No. 95 p 391-414, 1969 entitled "The production of cellulases".

An enzyme process converting cellulose to glucose and more useful by-products could, if it can be achieved effectively, give us glucose at moderate temperature and pH conditions in comparison with acid hydrolysis. Ultimately, glucose could be recovered as is done in the enzymatic hydrolysis of starch.

However, it was thought heretofore that enzymes are too expensive for the enzyme process to be realized.

The cost is mainly attributed to the facts that a cellulase can not hydrolyze a cellulose so easily as the amyloglucosidase does starch, and, therefore, a lot of enzyme is required to hydrolyze cellulose effectively, that activity of cellulase in culture broth is limited since the ability of a fungus to elaborate a cellulase is strongly repressed by the cellulose hydrolyzate comprising glucose, cellobiose and so on that is essential component for production of cellulase and may be added as such to the cellulase production medium and that the production of cellulase by culturing a fungus takes too long a time, for example, it takes more than 2 weeks for substantial production of cellulase by culturing T. viride.

Accordingly, it is an object of the present invention to provide a new thermostable cellulase hydrolyzing cellulose at an elevated temperature to produce glucose and other useful by-products and a method to produce the same economically.

Other and further objects and advantages of the invention will become apparent more fully from the following description.

A new thermostable cellulase has been found by the inventors in a culture broth of a fungus belonging to Sporotrichum cellulophilum, a new species established by the inventors.

The newly found thermostable cellulase hydrolyzes easily various types of microcrystalline cellulose such as Avicel and hydrocellulose, sulfite pulps such as Solka Floc, as well as filter paper and cotton fabrics and highly resistant crystalline cellulose such as cotton to produce mainly glucose and other useful by-products at elevated temperatures ranging from 60° to 65° C at a pH ranging from 4.0 to 7.5 effectively and the optimum pH of this cellulase for filter paper is about 6.0 at 60° C. The newly found thermostable cellulase is produced by a thermophilic fungus, Sporotrichum cellulophilum AJ 6986, recognized as new species, as explained below:

This fungus has been deposited under deposition No. FERM-P 3514 with, and is available from, the Fermentation Research Institute of the Agency of Industrial Science & Technology, Chiba-shi, Chiba-ken, Japan and also deposited under deposition No. ATCC 20494 with, and is available from, American Type Culture Collection, 12301 Parklawn Drive, Rockville, Maryland 20852, U.S.A.

This fungus is thermophilic and can grow even at 50° C and grows most rapidly at 40° C to 45° C.

More precise microbiological characteristics of the Sporotrichum cellulophilum isolate is as follows:

(1) Condition of growth on media

1. Colonies on yeast starch agar (YpSs: Cooney & Emerson (1964) Thermophilic fungi, Eumycota. San Francisco: W. H. Freeman Publ. Co.)

Colonies on YpSs agar growing rapidly attaining a diameter of 6.6 to 6.8 cm in 3 days at 45° C. Colonies are from floccose to more or less cottony, and produce spores abundantly. They produce drops of colorless water on loose texture. Color of colonies is at first white, then becomes pale yellowish orange through pale yellowish brown. Reverse of the colonies turns from yellowish gray to pale yellow in age. Mycelia are hyaline, smooth, branched, septated, and 1.5-5 nm in width. Aleuriospores are borne singly or gregarious on the side of mycelia or on the short aleuriophores or on the sterigmata. These aleuriospores are hyaline, smooth, monocellular and their cell walls are 0.25-5 nm in thickness, and their forms are from ovate to pyriform (4-5 × 2.5-3 nm), often elliptical ((4.5-) 5-8 × 2.5-4 nm). Each spore is 1-1.5 nm in width and has narrow scars.

2. Colonies of potato dextrose agar

Colonies on potato dextrose agar growing rapidly attaining a diameter of 6.3 to 6.5 cm in 3 days at 45° C. The colonies are floccose to more or less cottony and produce spores abundantly. They produce drops of colorless water all over the surface. The color of colonies becomes pale yellowish orange. Reverse of the colonies turns at first hyaline, becoming pale yellow through pale brown in age.

(2) Physiological properties

1. Range of growth on potato dextrose medium pH: 3 - 8 Temperature: 25 - 50° C

2. Optimum conditions for growth on potato dextrose medium pH: 4 - 7 Temperature: 35 - 45° C On the basis of the microbiological characteristics mentioned above, this isolate belongs to the genus of Sporotrichum. Only *Sporotrichum thermophile* is known as a thermophilic fungus among the genus of Sporotrichum. While, *S. thermophile* produces orange brown aleuriospores, surface of spores is smooth or irregular and it grows at temperatures from 25° to 55° C[1,2,3], the isolate produces hyaline spores, surface of spores is smooth, never irregular and it grows at temperatures from 25° to 50° C.

On the basis of color of aleuriospore, status of surface of spores and range of growth temperature, that are most important microbiological characteristics for taxonomy of fungi, the isolate differs distinctly from *S. thermophile*. Accordingly, the isolate is recognized as a new species of the genus Sporotrichum, and is named *Sporotrichum cellulophilum*.

(1) Apinis: Nova Hedwigia, 5, 57–78, (1963).

(2) Semeniuk & Carmichael: Can. J. Bact., 44, 105–108, (1966).

(3) Hedger & Hudson: Trans Br. Mycol. Soc., 54, 497–500, (1970).

S. cellulophilum AJ 6986 can grow rapidly at elevated temperatures as stated above, and, therefore, accumulates substantial amounts of cellulase within 2 or 4 days and the enzyme activity in the culture filtrate is as strong as that of T. viride is.

A mutant strain, S. cellulophilum AJ 6987, has been artificially induced by treating spores of the parent strain, S. cellulophilum AJ 6986, with N-methyl-N'-nitroso-N-nitrosoguanidine, which mutant can grow on a potato dextrose agar containing 0.05% of 2-deoxyglucose or 3-0-methylglucose on which the growth of the parent strain is completely inhibited, produces thermostable cellulase in the presence of 1.0% glucose and secretes three times the amount of cellulase produced by its parent.

The mutant strain has also been deposited with, and is available from, the same depositories, but under deposition No. FERM-P 3969 and ATCC 20493, respectively. S. cellulophilum grows well on a medium containing a usual carbon source such as sucrose, glucose and starch, but the cellulase is produced only when the fungus is grown on a medium containing cellulose or cellulose hydrolyzate such as cellobiose since the cellulase is an adapted enzyme and therefore, cellulose or cellulosic materials have to be added as inducers to the medium for producing the enzyme.

As the cellulosic materials for a culture medium for cellulase production, wood wastes such as sawdust, chips, paper refuse, agricultural wastes in the form of straws, leaves, stalks, hulls, shells, bagasses, soybean refuse, etc. are used preferably.

The culture medium contains a nitrogen source and inorganic salts besides the carbon source and, where required, minor organic nutrients are also added. These nitrogen source and inorganic salts are conventional and ammonium sulfate, ammonium nitrate, urea, amino acid, peptone and/or protein are used as nitrogen sources. As inorganic ions, $K^+$, $PO_4^{2-}$, $Mg^{2+}$, $Ca^{2+}$, $Co^{2+}$, $Mn^{2+}$, $Zn^{2+}$, $Fe^{2+}$, and/or $SO_4^{2-}$ may be used in the form of inorganic salts, when required.

While a solid culture method such as the Koji process used in Japan may be employed for the production of the cellulase, in which method wheat bran is steamed, piled in a tray and inoculated with a spore suspension and air is forced to circulate through the medium, a liquid culture method is preferable from the industrial point of view.

In a liquid culture method, the temperature of the culture medium is maintained at 40° to 50° C and the pH is maintained at 4.0 to 7.0. In proportion to the vigorous growth of S. cellulophilum, a substantial amount of thermostable cellulase is accumulated in the culture medium within 2 to 4 days. After 2 to 4 days culture, the culture broth is filtrated off or centrifugated to remove the insoluble residue mainly consisting of mycelium of the fungus.

The activity of the thermostable cellulase is measured by determining the production of reducing sugar expressed as glucose by the dinitrosalicylic acid (DNS) method as follows (a) Filter Paper assay procedure (F.P. activity):

To 50 mg (1 × 6 cm) of Whatman No. 1 filter paper, 1.0 ml of 0.05M, pH 6.0 citrate buffer and 0.5 ml of the tested enzyme solution are added in the order. The mixture is incubated 1 hour at 60° C and heated in boiling water for 5 minutes. Thereafter, 3.0 ml of DNS reagent is added, and the mixture heated in boiling water for 5 minutes. To the heated colored mixture, 16.0 ml of water is added and an increase in absorbance at 550 nm is determined.

(b) Crude Cellulosic Material assay procedure (C.C.M. activity)

This procedure is carried out by using a crude cellulosic material of soybean (C.C.M.S.) as substrate instead of Whatman No. 1 filter paper in the above mentioned Filter paper assay procedure. The substrate (C.C.M.S.) is prepared from defatted soybean by alkaline extraction, as follows:

To defatted soybean, a large amount of 0.2N-NaOH is added and the mixture is heated at 80° C for 16 hours. After the alkaline extraction the insoluble residue of C.C.M.S. is recovered by separating it by filtration, washing with water and drying in vacuo. C.C.M.S. thus prepared consists of 33% by weight of crude cellulose and 25% by weight of hemicellulose.

One unit of cellulase activity is defined in the present invention as the ability of producing the reducing sugar equivalent to 1.0 μg of glucose per hour at pH 6.0 and 60° C.

The cellulase activity in the freshly obtained filtrate of S. cellulophilum AJ 6986 is about 15,000 to 30,000 U/ml (FP activity) and 40,000 to 50,000 U/ml (C.C.M. activity).

The FP activity in filtrate of S. cellulophilum AJ 6987 (mutant strain) reaches 50,000 to 80,000 U/ml which is 3–4 times that produced by the parent strain.

The culture filtrate may be used as such directly as the enzyme source without further purification, but, where required, a crude enzyme preparation is easily prepared from the culture filtrate by conventional methods such as salting out with ammonium sulfate or sodium sulfate and precipitation by an organic solvent such as acetone, ethanol or isopropanol. If further purification is desired, the crude enzyme is purified by ion exchange or gel filtration.

Crude enzyme preparation obtained by the salting out or precipitation from the culture filtrate of S. cellulophilum AJ 6986 or its mutant strain AJ 3987 has the following chemical and physical properties:

(1) Substrate:

The cellulase hydrolyzes various types of microcrystalline cellulose such as Avicell, hydrocellulose, sulfite pulp such as Solka Floc, as well as filter paper and cotton fabrics and highly resistant crystalline cellulose such as cotton to produce mainly glucose, a small amount of cellobiose and other useful by-products and it also hydrolyzes cellulosic material contained in paper refuse, paper mill effluent, sawdust, sludges, grasses, straw, bagasse, hulls and stalks etc. to convert them to glucose and other useful by-products.

(2) Optimum pH

The optimum pH of the cellulase for filter paper is about 6.0 at 60° C as shown in FIG. 1. FIG. 1 shows relative cellulase activity against maximum activity. In each test, Whatman No. 1 filter paper is hydrolyzed at 60° C for 1.0 hour in 0.05 M citrate buffer solution having the indicated pH.

(3) pH stability

The cellulase is stable at a pH ranging from 4.0 to 7.0 when heated at 50° C for 4.0 hours without any substrate and more than 50% of the activity remains after such heating.

(4) Optimum temperature

As illustrated in FIG. 2, the optimum temperature for activity of the cellulase is from 60° to 65° C. In each test, Whatman No. 1 filter paper is hydrolyzed at pH 6.0 for 1 hour in 0.05 M phosphate buffer solution.

(5) Heat stability

The cellulase of the present invention is thermostable compared with that of Trichoderma viride.

While the cellulase of Trichoderma viride is inactivated almost completely when heated at 50° C, the cellulase of the present invention is quite stable as shown in FIG. 3. FIG. 3 shows residual cellulase activity in percent of the initial activity. In each test, the crude enzyme preparation is dissolved in 0.05 M, pH 6.0, phosphate buffer solution (0.1 g/dl), heated at 50° C, 60° C, or 80° C for 1 to 3 hours without substrate. After each heating treatment, each residual cellulase activity to Whatman No. 1 filter paper is determined by incubation at 60° C for 1 hour.

Shortly before Apr. 30, 1976, it had been reported that another thermostable cellulase had been produced by another thermophilic fungus belonging to the Family of the Chaetomiaceae by F. Tokuyama and W. A. Skinner in Abstract Annual of Meeting of the Agricultural Chemical Society of Japan, 188, 189, 1975 (in Japanese), in which it is also reported that its optimum temperature for hydrolyzing cellulose ranges from 60° C to 65° C and its optimum pH is 5.0.

The thermostable cellulase of the present invention hydrolyzes at a broad pH range from 4.0 to 7.5 effectively and its optimum pH to Whatman No. 1 filter paper is 7.0 at 45° C and shifts to 6.0 at 60° C, and, therefore, the cellulase appears different from that of the Chaetomiaceae and has the advantage of hydrolyzing cellulose at a wide pH range.

EXAMPLE 1

50 ml of an aqueous culture medium of which the pH was 6.0, containing 0.2 g/dl cellulose powder, 0.2 g polypeptone, 0.15 g $KH_2PO_4$, 0.03 g $(NH_4)_2SO_4$, 0.03 g $MgSO_4 \cdot 7H_2O$, 0.1 g $CaCl_2$, 0.1 g TWeen 80 (polyoxyethylene sorbitan mono-oleate, manufactured by Chemical Industries) and 0.1 ml/dl of minor element solution (which contains, per deciliter, 1.5 g $ZnSO_4 \cdot 7H_2O$, 0.5 g $FeSO_4 \cdot 7H_2O$, 20 mg $CoCl_2$, and 10 mg $MnSO_4 \cdot 4H_2O$) was put into a 500 ml shake flask and heated at 120° C for 10 minutes.

Sporotrichum cellulophilum AJ 6986 grown on potato dextrose agar slant at pH 6.0 and 45° C for 2 days was inoculated in the sterilized culture medium and cultured at 48° C for 2 days with shaking (115 Oscill./min. 7.0 cm in width).

The culture broth thus obtained was centrifuged to remove the insoluble residue (mainly consisting of fungus mycelium). The cellulase activity of the supernatant liquid was 13,000 U/ml (as F.P. activity) and 23,160 U/ml (as C.C.M. activity).

EXAMPLE 2

300 ml culture medium having a pH of 6.0 and containing, per deciliter, 1.0 g $KH_2PO_4$, 0.2 g $(NH_4)_2SO_4$, 0.03 g $MgSO_4 \cdot 7H_2O$, 0.03 g $CaCl_2$ and "OKARA" (a water-extracted residue of defatted soybean containing 30% by weight of total sugar, 30% of crude protein and 10% of crude cellulosic material) was put into a 1 l fermenter vessel and sterilized at 115° C for 10 minutes. S. cellulophilum AJ 6986 grown in the same manner as described in Example 1 was inoculated and cultured at 47° C for 2 days with aeration (1.0 l/min.) under pressure of 0.5 kg/cm² with stirring by impeller, the impeller speed through the culture being kept at 300 r.p.m.

The culture broth was filtered through glass wool to remove the insoluble residue and 280 ml culture filtrate was obtained, of which the cellulase activity was 29,800 U/ml (FP activity) and 50,100 U/ml (C.C.M. activity).

1.0 g of Whatman No. 1 filter paper was completely dissolved by a 10 ml portion of this culture filtrate during incubation at pH 6.0 for 20 hours.

To another 250 ml portion of the culture filtrate, 150 g solid ammonium sulfate was added and dissolved, and the resulting solution was left to stand overnight below 10° C. The crude enzyme thus precipitated was separated from the liquid by centrifugation (10,000 r.p.m. for 10 minutes) and dried under reduced pressure.

The dried crude enzyme preparation weighed 5.0 g and its cellulase activity was $1.1 \times 10^6$ units per gram (as F.P. activity).

EXAMPLE 3

S. cellulophilum AJ 6987, a mutant strain of S. cellulophilum AJ 6986, was grown on potato dextrose agar slant (pH 6.0) at 45° C for 2 days and inoculated in a culture medium prepared as described in Example 1 and cultured at 48° C for 4 days with shaking (115 Oscill./min.).

The culture broth was filtered and the cellulase activity of the culture filtrate was 52,000 U/ml (as F.P. activity).

What is claimed is:

1. A cellulase produced by Sporotrichum cellulophilum and having the following properties:
    (a) hydrolyzes microcrystalline cellulose, hydrocellulose, sulfite pulp, filter paper, and cotton mainly to glucose and to a small amount of cellobiose;
    (b) optimum activity on Whatman No. 1 filter paper at pH 5.5 to 6.5 and at 60° C.;
    (c) optimum activity at 60° to 65° C.;
    (d) more than 50% of initial activity is retained at 50° C for 4 hours at any pH from 4.0 to 7.0;
    (e) stable when heated without any substrate at 50° C.;
    (f) retaining more than 40% of initial activity when heated at 80° C. for 1 hour without any substrate.

2. A method for producing the cellulase set forth in claim 1, which comprises culturing a strain of the fungus Sporotrichum cellulophilum capable of producing said cellulase in a culture medium until a substantial amount of said cellulase is accumulated in said culture medium, and recovering the accumulated cellulase.

3. A method as set forth in claim 2, wherein the said fungus is Sporotrichum cellulophilum FERM-P 3514 ATCC 20494.

4. A method as set forth in claim 2, wherein the said fungus is an artificially induced mutant of Sporotrichum cellulophilum which is capable of growing on a medium containing 2-deoxyglucose or 3-0-methylglucose.

5. A method as set forth in claim 4, wherein the said mutant is Sporotrichum cellulophilum FERM-P 3969 ATCC 20493.

* * * * *